United States Patent
Carson et al.

(10) Patent No.: US 9,566,185 B2
(45) Date of Patent: Feb. 14, 2017

(54) SYSTEM AND METHOD FOR PATIENT TEMPERATURE CONTROL

(75) Inventors: Gary A. Carson, Golden, CO (US); Gary Gruszecki, Golden, CO (US); Robert Proctor, Lakewood, CO (US)

(73) Assignee: Medivance Incorporated, Louisville, CO (US)

( * ) Notice: Subject to any disclaimer, the term of this patent is extended or adjusted under 35 U.S.C. 154(b) by 2029 days.

(21) Appl. No.: 12/250,320

(22) Filed: Oct. 13, 2008

(65) Prior Publication Data

US 2009/0099629 A1    Apr. 16, 2009

Related U.S. Application Data

(60) Provisional application No. 60/979,760, filed on Oct. 12, 2007.

(51) Int. Cl.
*A61F 7/00* (2006.01)

(52) U.S. Cl.
CPC .............. *A61F 7/0085* (2013.01); *A61F 7/00* (2013.01); *A61B 34/25* (2016.02); *A61F 2007/0054* (2013.01); *A61F 2007/0086* (2013.01); *A61F 2007/0093* (2013.01); *A61F 2007/0095* (2013.01); *A61F 2007/0096* (2013.01)

(58) Field of Classification Search
CPC .............. A61F 7/00; A61F 2007/0054; A61F 2007/0086; A61F 2007/0093; A61F 2007/0095; A61F 2007/0096
See application file for complete search history.

(56) References Cited

U.S. PATENT DOCUMENTS

| 4,844,072 A | 7/1989 | French et al. |
| 4,961,422 A | 10/1990 | Marchosky et al. |

(Continued)

FOREIGN PATENT DOCUMENTS

| EP | 0757907 A1 | 2/1997 |
| EP | 0846440 A2 | 6/1998 |

(Continued)

*Primary Examiner* — Laura Bouchelle
*Assistant Examiner* — Anh Bui
(74) *Attorney, Agent, or Firm* — Marsh Fischmann & Breyfogle LLP

(57) ABSTRACT

A patient temperature control system and method are provided for automated temperature control according to a programmed protocol. In one aspect, at least one programmed protocol may be established for each of a plurality of patient thermal therapy phases. In turn, the temperature of a thermal exchange medium may be controlled, based at least in part, upon the programmed protocol, during each of the phases. In another aspect, a plurality of programmed protocols may be established, wherein a selected one of the protocols (e.g. selected by a user at a user interface) may be utilized for automated temperature control during patient thermal therapy. The protocol(s) may include a target patient temperature and/or a set duration for one or more of the phase of thermal therapy. Further, the protocol(s) may be user-definable and modifiable during therapy. In a multi-phase configuration, automatic termination and initiation of successive phases may be selectively established by a user, based on target patient temperature data and/or set duration data on a phase-specific basis.

36 Claims, 15 Drawing Sheets

(56) References Cited

U.S. PATENT DOCUMENTS

| | | |
|---|---|---|
| 5,266,778 A | 11/1993 | Bailey |
| 5,385,529 A | 1/1995 | Koch |
| 5,871,526 A | 2/1999 | Gibbs et al. |
| 6,149,674 A | 11/2000 | Borders |
| 6,197,045 B1 | 3/2001 | Carson |
| 6,231,594 B1 | 5/2001 | Dae |
| 6,238,354 B1 | 5/2001 | Alvarez |
| 6,375,674 B1 | 4/2002 | Carson |
| 6,436,130 B1 | 8/2002 | Philips et al. |
| 6,454,792 B1 | 9/2002 | Noda et al. |
| 6,517,510 B1 | 2/2003 | Stewart et al. |
| 6,582,457 B2 | 6/2003 | Dae et al. |
| 6,620,187 B2 | 9/2003 | Carson et al. |
| 6,620,189 B1 | 9/2003 | Machold |
| 6,645,232 B2 | 11/2003 | Carson |
| 6,648,905 B2 | 11/2003 | Hoglund et al. |
| 6,660,027 B2 | 12/2003 | Gruszecki et al. |
| 6,669,715 B2 | 12/2003 | Hoglund et al. |
| 6,692,518 B2 | 2/2004 | Carson |
| 6,699,267 B2 | 3/2004 | Voorhees et al. |
| 6,702,839 B1 | 3/2004 | Dae et al. |
| 6,802,855 B2 | 10/2004 | Ellingboe et al. |
| 6,818,012 B2 | 11/2004 | Ellingboe |
| 6,827,728 B2 | 12/2004 | Ellingboe et al. |
| 6,921,198 B2 | 7/2005 | Gruszecki et al. |
| 7,008,444 B2 | 3/2006 | Dae et al. |
| 7,294,112 B1 | 11/2007 | Dunlop |
| 7,361,186 B2 | 4/2008 | Voorhees et al. |
| 7,827,815 B2 | 11/2010 | Carson et al. |
| 7,867,266 B2 | 1/2011 | Collins |
| 8,047,010 B2 | 11/2011 | Carson et al. |
| 8,647,374 B2 | 2/2014 | Koewler |
| 9,314,367 B2 | 4/2016 | Callister et al. |
| 2003/0078639 A1* | 4/2003 | Carson ............... A61F 7/0085 607/104 |
| 2004/0122559 A1 | 6/2004 | Young et al. |
| 2005/0234532 A1 | 10/2005 | Eggers et al. |
| 2006/0069418 A1* | 3/2006 | Schock ............... A61F 7/00 607/104 |
| 2007/0129622 A1 | 6/2007 | Bourget et al. |
| 2007/0191918 A1 | 8/2007 | MacHold et al. |
| 2009/0018627 A1* | 1/2009 | Levinson ............ A61F 7/10 607/96 |
| 2009/0131835 A1 | 5/2009 | Voorhees et al. |
| 2010/0152822 A1* | 6/2010 | Callister et al. ............ 607/105 |

FOREIGN PATENT DOCUMENTS

| | | |
|---|---|---|
| JP | 2005-518837 A | 6/2005 |
| WO | 9636950 A1 | 11/1996 |

* cited by examiner

| SETUP PROTOCOL | EDIT TITLE | C/F DEFAULT | HELP |
| --- | --- | --- | --- |
| | MODIFIABLE | C/F SELECTABLE | CONTROL STRATEGY 2 |
| | | | PATIENT TEMP 2 |

1. DR. JONES SCA ▽

PHASE 1 ▽

MANUAL ▽

| | | |
| --- | --- | --- |
| 280a { | 4.0C | WATER TARGET |
| | 1:00HR  282a | DURATION |
| | Y N | JUMP TO NEXT PHASE AT DURATION |
| | Y N | JUMP WHEN PATIENT TEMP OK |
| | 40.0C | PATIENT HIGH ALERT |
| | 33.0C | PATIENT LOW ALERT |

HELP TEXT:
THIS PROTOCOL FOR SUDDEN CARDIAC ARREST PATIENTS IN THE NEURO ICU FLOOR 5. DO NOT USE FOR IN-HOSPITAL ARRESTS. USE DR. SMITHS PROTOCOL INSTEAD. FOLLOW SEDATION PROTOCOL #1234. CALL DR. JONES AT 555-1234 IF PROBLEMS.

CANCEL
SAVE AS
DEFAULT
SAVE THIS
CASE ONLY

FIG.3H

| SETUP PROTOCOL | EDIT TITLE | C/F DEFAULT | HELP |
|---|---|---|---|
| 1. DR. JONES SCA ▽ | MODIFIABLE | C/F SELECTABLE | CONTROL STRATEGY 2 |
| | | | PATIENT TEMP 2 |

PHASE 1 ▽
AUTOMATIC ▽
- 37.0 C — PATIENT TARGET
- 6:00 HR — DURATION
- T D N — JUMP TO NEXT PHASE / AT TARGET/DURATION/NO
- 42.0 C — WATER HIGH LIMIT
- 4.0 C — WATER LOW LIMIT
- 40.0 C — PATIENT HIGH ALERT
- 33.0 C — PATIENT LOW ALERT

HELP TEXT:
THIS PROTOCOL FOR SUDDEN CARDIAC ARREST PATIENTS IN THE NEURO ICU FLOOR 5. DO NOT USE FOR IN-HOSPITAL ARRESTS. USE DR. SMITHS PROTOCOL INSTEAD. FOLLOW SEDATION PROTOCOL #1234. CALL DR. JONES AT 555-1234 IF PROBLEMS.

CANCEL
SAVE AS DEFAULT
SAVE THIS CASE ONLY

FIG. 3I

SYSTEM AND METHOD FOR PATIENT TEMPERATURE CONTROL

RELATED APPLICATIONS

This application claims priority to U.S. Patent Provisional Application Ser. No. 60/979,760, filed Oct. 12, 2007, entitled "SYSTEM AND METHOD FOR PATIENT TEMPERATURE CONTROL", the entirety of which is hereby incorporated by reference.

FIELD OF THE INVENTION

The present invention relates to an improved system and method for patient temperature control via temperature control of a thermal exchange medium, including automated thermal control of a plurality of therapy phases based upon one or more programmed protocols.

BACKGROUND OF THE INVENTION

The therapeutic use of bodily cooling and heating systems, respectively, is ever-increasing. Hypothermia may occur for a variety of reasons, including exposure to cold environments, or complex surgical procedures.

During surgery, a patient typically experiences mild hypothermia as a result of the effect of general anesthesia on the body's thermoregulatory system and prolonged exposure of internal organs. Mild hypothermia in a surgical patient has been thought to prolong the time to extubation, contribute to coagulopathies, increase the chance of infection, and increase cardiac demand as a result of shivering. In such procedures, controlled patient warming may be of therapeutic benefit.

Hyperthermia may occur as a result of stroke, cardiac arrest and head trauma. In such cases it is now accepted that rapid cooling can yield significant therapeutic benefits. Specifically, research indicates that even though a stroke or cardiac arrest victim's brain cells may loose their ability to function, the cells do not necessarily die quickly. In fact, brain damage from a stroke or cardiac arrest may take hours to reach maximum effect. Neurological damage may be reduced and the stroke or cardiac arrest victims' outcome improved if a neuroprotectant therapy is applied within this time frame.

Similarly, elements in the genesis of a traumatic brain injury (e.g., resulting from falls, vehicular accidents and the like) are now understood to overlap with elements in the genesis of neurological damage in stroke victims. In particular, delayed secondary injury at the cellular level after the initial head trauma is now recognized as a measured contributing factor to the ultimate tissue loss that occurs after brain injury. Again, neurologic damage may be reduced if a neuroprotectant therapy is rapidly applied. Further, in this regard, studies have shown that treatment with mild hypothermia, defined as lowering core body temperature at 2-3° C. confers neuroprotection in stroke victims, and may hasten the neurologic recovery and improve outcomes when applied for 12-72 hours in cases of traumatic head injury. Again, to optimize such therapies, the neuro-protective therapy should be initiated as soon as possible after a stroke or traumatic head injury.

As reflected by the foregoing, significant therapeutic benefits may be realized through the use of bodily cooling and heating systems. In turn, systems which offer enhanced operational features are of particular interest as cooling/heating therapy modalities continue to evolve.

SUMMARY OF THE INVENTION

One objective of the present invention is to provide a patient temperature control system and method that facilitates enhanced reliability.

Another objective of the present invention is to provide an improved patient temperature control system and method that is user friendly.

Yet another objective of the present invention is to provide an improved patient temperature control system and method that facilitates the realization of enhanced efficiencies of medical care resources.

One or more of the noted objectives and additional advantages may be realized by the system and method of the present invention. The inventive system may be computer-based to include a user interface for receiving user control input and for providing corresponding output signals to a programmable control module.

In one aspect, the programmable control module may be provided to store control data and apply control logic in the generation of control signals in corresponding relation to a plurality of different patient temperature control phases (e.g. two or more). In this regard, a programmable multi-phase control module may be provided to facilitate the establishment of one or more protocols that each comprise parameter data for use in the control of patient temperature in each of the plurality of a patient temperature phases.

In another aspect, the programmable control module may be provided to facilitate the establishment of and to store two or more programmed protocols comprising control data, wherein the programmable control module may utilize a selected protocol and apply control logic in the generation of control signals in a patient thermal therapy procedure comprising one or more phases. In this regard, the user interface may be provided to facilitate the establishment of multiple programmed protocols, and to allow a user to a select a given one of the protocols for application in a given patient therapy. By way of example, a plurality of protocols may be pre-established via the user interface, wherein such protocols are each directed to different patient treatment applications and/or protocol preferences of medical personnel.

The protocol data for a given phase may comprise a target patient temperature. Alternatively or additionally, the protocol data for a given phase may comprise a set duration. In one arrangement, the user interface may be adapted to receive user input to establish the protocol data.

For each given protocol, the programmable control module may be adapted to provide output control signals to a thermal exchanger. In turn, the thermal exchanger may be provided to responsively change the temperature of a thermal exchange medium to achieve a desired thermal exchange with a patient. By way of example, the thermal exchange medium may comprise a fluid (e.g. a circulated liquid and/or gas), wherein componentry of the thermal exchanger operates to change the temperature of the thermal exchange medium in corresponding relation to control signals output from the programmable control module.

The patient temperature control system may also include a temperature sensor to sense the temperature of a patient on an ongoing basis and provide a corresponding output signal to the programmable control module. In turn, the programmable control module may utilize the patient temperature measurement signal and target patient temperature protocol data to generate control signals (e.g. on a single phase or phase specific basis). Further, the programmable control module may further employ phase duration protocol data in conjunction with the generation of control signals (e.g. on a single phase or phase specific basis).

The user interface and programmable control module may also be adapted to allow for selective user modification of target patient temperature data and/or phase duration data (e.g. on a single phase or phase specific basis). In turn, a modified protocol may be employed by the programmable control module during any remaining portion of a modified phase.

The user interface may be further adapted with various numerical and graphic user interface functionalities. For example, a graphic display may be provided to visually present plots of target patient temperature adjustment rates for one or more patient treatment phases, together with a plot(s) of a measured patient temperature and/or of a measured temperature of a thermal exchange medium. As may be appreciated, such visual display facilitates medical personnel monitoring of a given patient therapy procedure so as to enhance overall control and responsive action as necessary.

In conjunction with the present invention, an inventive method is also provided for controlling a temperature of a thermal exchange medium in a thermal patient temperature control system. Correspondingly, the method provides for patient temperature control.

The inventive method may comprise a step of establishing a programmed protocol for at least one phase of patient thermal therapy. The method may further include a step of controlling automatically the temperature of a thermal exchange medium of a patient temperature control system, based at least in apart on the programmed protocol, for at least a portion of each of the at least one phase.

In one aspect, the programmed protocol may be established to comprise a target patient temperature and/or a set duration for a plurality of phases of patient thermal therapy. Such phases may be successive or may have one or more therapy phases therebetween.

In another aspect, the establishing step may be repeated a plurality of times so as to result in a plurality of programmed protocols. In turn, the method may include a step of selecting (e.g. by a user at a user interface) one of the plurality of programmed protocols for application in the controlling step.

The controlling step may entail setting the temperature of the thermal exchange medium based at least in part upon a measured patient temperature and a corresponding target patient temperature for a given phase. By way of example, the temperature of the thermal exchange medium may be set (e.g. cooled, maintained or heated) pursuant to a comparison of the measured patient temperature and the corresponding target patient temperature.

In another aspect, a programmed protocol may be established for at least two successive phases of patient treatment. In turn, the controlling step may further provide for the automatic termination and initiation, respectively, of first and second ones of the at least two successive phases in response to a comparison of a measured patient temperature and a target patient temperature for the first one of the two successive phases. In another approach, automatic termination and initiation, respectively, of successive phases may occur upon the expiration of a set phase duration comprising the programmed protocol.

In various applications, the programmed protocol may be established to comprise different target patient temperatures for at least a first set of two of the plurality of phases. Additionally, the programmed protocol may be established to comprise the same target patient temperature for at least a second set of two of the plurality of phases. In one embodiment, the plurality of phases may include at least three successive phases, wherein the target patient temperatures for the three phases are established so as to affect a desired degree of patient cooling/heating during a first phase, maintain the patient at a cooled/heated temperature during a second phase, and heat/cool a patient at desired rate during a third phase of treatment.

Numerous additional aspects and advantages will be apparent to those skilled in the art upon consideration of the further description of embodiments hereinbelow.

BRIEF DESCRIPTION OF THE DRAWINGS

FIGS. 3A-3I illustrate exemplary screens of one embodiment of a user interface employable in the system embodiment of FIG. 1 and method embodiment of FIG. 2.

DETAILED DESCRIPTION

Figure 1:
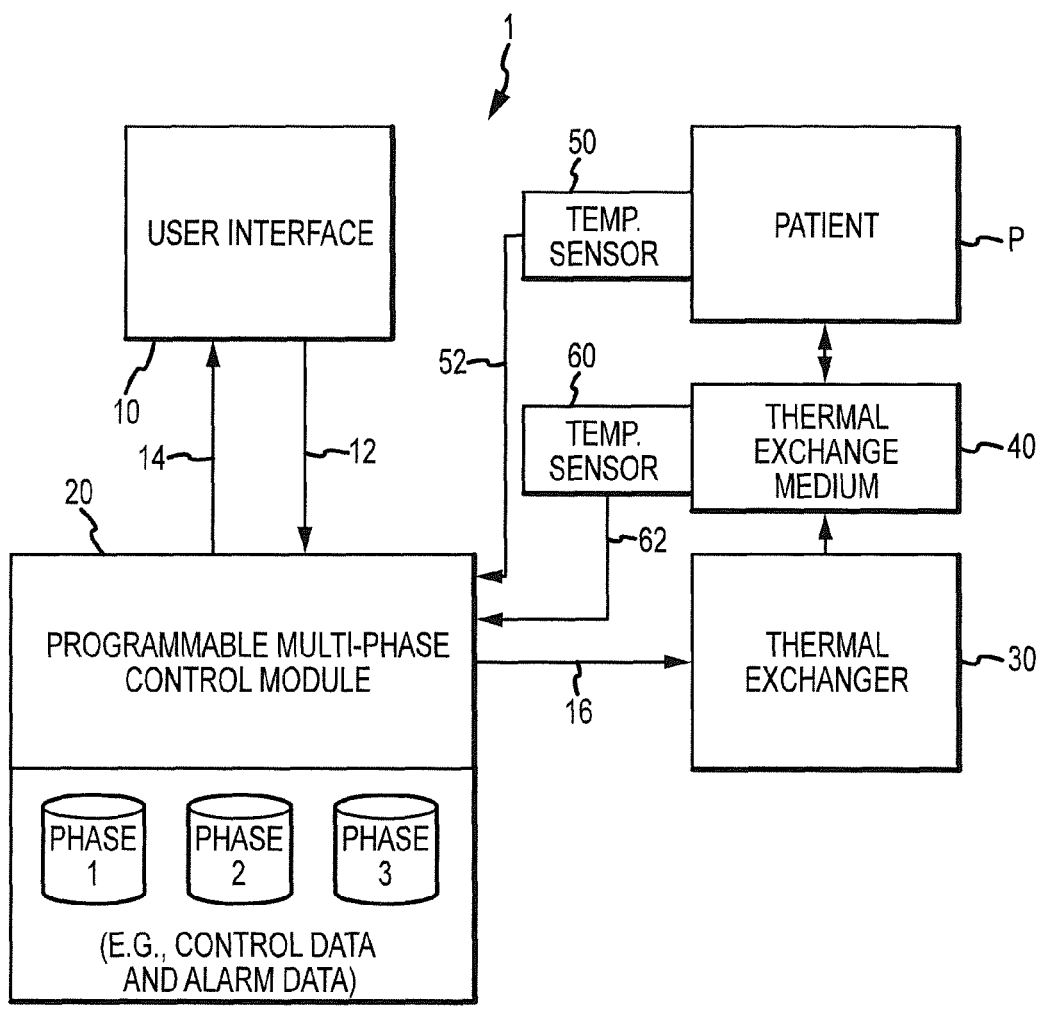
FIG. 1 illustrates one embodiment of a patient temperature control system comprising the present invention.

FIG. 1 illustrates one embodiment of a patient temperature control system 1 comprising the present invention. The patient temperature control system 1 may be computer-based to include a user interface 10 for receiving user control input and for providing corresponding signals 12 to a programmable control module 20. User interface 10 may be further adapted to receive signals 14 from the programmable control module 20 for use in the display of control and measured data and for operative, interactive interface with a user at user interface 10. In the later regard, user interface 10 may include an interactive display as further described hereinbelow.

The programmable control module 20 may be provided to store data and generate signals in corresponding relation to a plurality of different patient temperature control phases. Additionally or alternatively, the programmable control module 20 may be provided to facilitate the establishment of one or more programmed protocols that each comprise parameter data for use in the control of each of the plurality of patient temperature control phases. By way of example, the protocol may comprise target patient temperature data for each of a plurality of treatment phases. Further, for one or more of the phases, the protocol may comprise a set duration for thermal treatment.

For each given protocol the programmable control module 20 may provide output control signals 16 to a thermal exchanger 30 on a phase-specific basis. In turn, thermal exchanger 30 may be provided to responsively change the temperature of a thermal exchange medium 40 to affect a desired thermal exchange, e.g. to cool, maintain the temperature of, or heat a patient. For example, thermal exchange medium 40 may comprise a fluid (e.g. a liquid and/or gas), and thermal exchanger 30 may comprise heating and/or cooling componentry which operate to change the temperature of the thermal exchange medium 40 in corresponding relation to control signals 16 output from the programmable control module 20.

In one approach, the programmable control module 20 may be provided for cooling/heating and circulating water as a thermal exchange medium 40 through one or a plurality of fluidly interconnected pads designed for intimate contact with and thermal energy exchange with a patient P, as taught in one or more U.S. Pat. No. 6,669,715 to Hoglund et al.; U.S. Pat. No. 6,827,728 to Ellingboe et al.; U.S. Pat. No. 6,375,674 to Carson; and U.S. Pat. No. 6,645,232 to Carson, all of which are here by incorporated by reference in their entirety.

As illustrated in FIG. 1, the patient temperature control system 1 may further comprise a temperature sensor 50 for measuring the temperature of the thermal exchange medium 40 on an ongoing basis and providing a corresponding output signal 52 to the programmable control module 20. Further, a temperature sensor 60 may be provided to measure the temperature of a patient P on an ongoing basis and provide a corresponding output signal to the programmable control module 20. The temperature sensor 60 may comprise a sensor to measure a core body temerature of the patient P. The output signals 52 and 62 may be employed by the programmable control module 20, together with protocol data and preset algorithms, to generate (e.g. via a processor and/or logic circuit) the control signals 16 provided to thermal exchange 30, so as to yield the desired temperature of thermal exchange medium 40 (e.g. on a single phase or phase specific basis).

Figure 2:
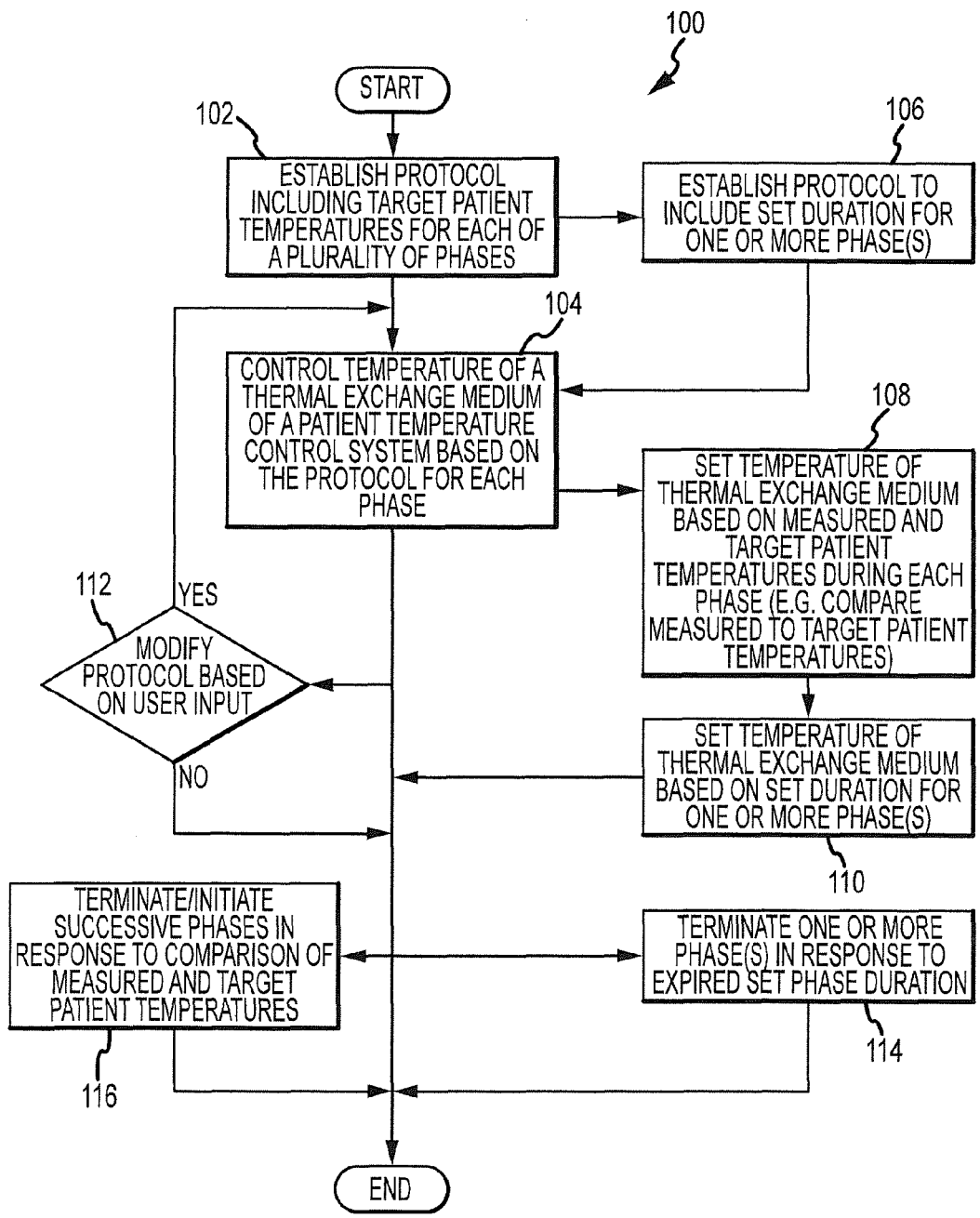
FIG. 2 illustrates one embodiment of a method for controlling the temperature of a patient via control of the temperature of a thermal exchange medium included in a temperature control system.

FIG. 2 illustrates one embodiment of a method 100 for controlling the temperature of a patient via control of the temperature of a thermal exchange medium included in a multi-phase temperature control system. As illustrated, the method 100 may include an initial step 102 of establishing a protocol that includes target patient temperatures for a plurality of phases (e.g. 2 or more phases having different patient temperature exchange objectives). Such phases may be successive in time and/or spaced in time. The establishment of a protocol may be achieved via use of the programmable control module 20 and operatively interconnected user interface 10 of FIG. 1.

By way of example, the protocol may be established to include target patient temperatures for at least three phases. Such an approach facilitates a procedure in which a patient is cooled/heated to a first target patient temperature in a first phase of therapy, maintained at or within a predetermined range of a second target patient temperature during a second phase (e.g. equal or different than the first target temperature), and heated/cooled to a third target patient temperature during a third phase. In other embodiments, following a third phase of therapy it may be desirable to establish a fourth target patient temperature for use in temperature control during a fourth phase of therapy.

The method may further include a step 104 of controlling the temperature of a thermal exchange medium of a patient temperature control system based on the protocol for each of the plurality of phases, e.g. via control of the thermal exchange 30 to control the temperature of the thermal exchange medium 40 of FIG. 1. In this regard, the protocol may be further established at step 106 so as to include a set duration for one or more of the phases, e.g. via use of a programmable control module 20 and user interface 10 of FIG. 1. In turn, the controlling step 104 may be carried out during such phase(s) for a duration(s) that correspond with the set duration.

In one approach, the controlling step 104 may be carried out in step 108 for each phase by setting the temperature of the thermal exchange medium based upon a measured patient temperature and the target patient temperature for such phase, e.g. via use of a signal from temperature sensor 50 by the programmable control module 20 of FIG. 1. By way of example, the patient temperature may be measured on an ongoing basis during a given phase and compared to the corresponding target patient temperature for such phase. Based upon such comparison, a patient temperature control system may provide for cooling and/or heating of a thermal exchange medium according to any of a plurality of pre-set algorithms, e.g. via control of the heat exchanger 30 by the programmable multi-phase control module 20 of FIG. 1.

In one approach, a control algorithm may provide for simply turning on/off a cooling/heating component of a temperature control system in intervals that depend upon a degree of difference reflected by comparison of the measured patient temperature and target patient temperature. In another approach, a control algorithm may provide for controlling an output magnitude of a cooling/heating component of a temperature control system based upon a degree of difference reflected by comparison of the measured patient temperature and target patient temperature.

In another approach, the controlling step 104 may be completed as step 110 for a given phase by setting the temperature of a thermal exchange medium based upon a measured patient temperature, a target patient temperature for such phase, and a set duration for such phase. For example, utilization of the noted parameters accommodates the determination and control use of a target patient temperature adjustment rate for the phase, wherein gradual patient cooling/warming over a desired time period may be facilitated.

In yet another approach, a measured thermal exchange medium temperature may be employed together with a measured patient temperature and target patient temperature to control the heating/cooling of a thermal exchange medium. Such an approach may yield enhanced system response.

The illustrated method 100 may further provide for modification of a given protocol based on user input at step 112, e.g. user input at the user interface 10 of FIG. 1. In this regard, a modified protocol may be employed for the remaining duration of a modified phase(s) and any for phase(s) that have not yet been initiated.

In the illustrated method, a given phase may be automatically terminated at step 114 by expiration of a corresponding set duration included within the programmed protocol for such phase. In this regard, the termination of a given phase may generally correspond with a change in the mode (e.g. cooling or heating) or a change in the magnitude of thermal exchange between a thermal exchange medium and a patient.

Method 100 may also provide for the termination and initiation of successive phases at step 116 in response to a comparison of a measured patient temperature and a target patient temperature. That is, upon determining that a target patient temperature has been reached during a given phase (e.g. via comparison of a measured patient temperature and a target patient temperature for an initial phase of treatment), such phase may be automatically terminated and a successive phase automatically initiated. Alternatively and/or additionally, the method 100 may also provide for the termination and initiation of successive phases in response to the expiration of a set duration for a first one of the two successive phases. The automatic phase termination/initiation features may be selectively established by a user for a given protocol on a phase-specific basis.

FIGS. 3A-3I illustrate an embodiment of an interactive user interface 200 operatively interconnected to a programmable multi-phase control module (e.g., module 20 of FIG. 1) for providing phase-related control and alarm data, and measured data, to a user and for prompting and receiving user control input via interactive screen displays. This embodiment contemplates one implementation of the present invention for patient cooling, e.g. for use in treating stroke, cardiac arrest and/or traumatic brain injury. Such embodiment is described for purposes of illustration and it should be understood that additional embodiments directed to patient cooling for other conditions (e.g. high fever) and/or patient warming may utilize features analogous to those described herein.

Figure 3A:
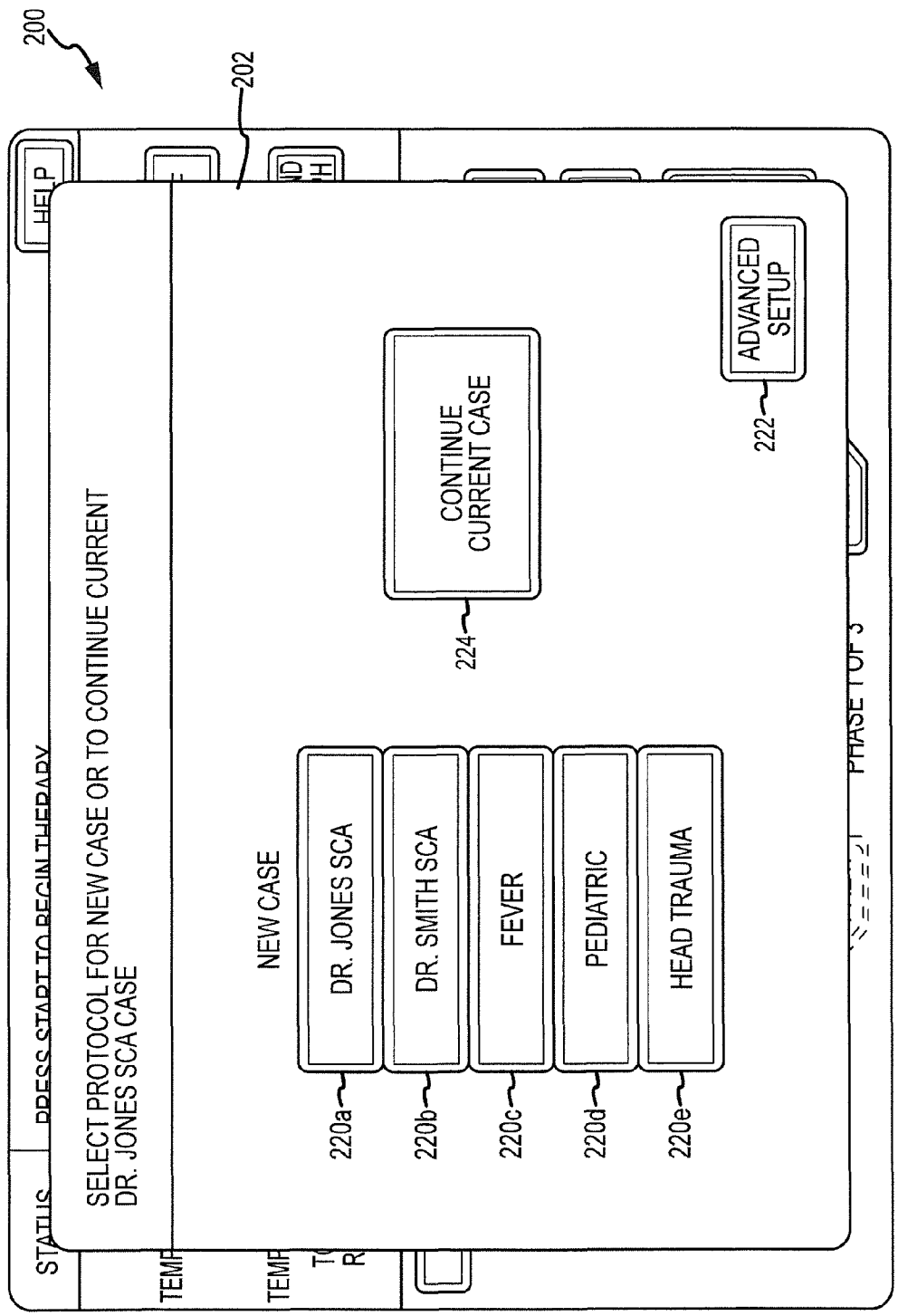

With particular reference to the interactive screen 202 of user interface 200 illustrated in FIG. 3A, a plurality of pre-established protocols options may be presented to a user, wherein any one of the protocol options may be selected for use in a given therapy. By way of example, each of the protocol options may be identified (e.g. by a given name) in corresponding spatial relation to an input selection button, wherein a user may select a mgiven one of a plurality of protocol option buttons 220a, 220b, 220c, 220d or 220e, e.g. via touch-screen and/or point-and-click functionality.

Figure 3B:
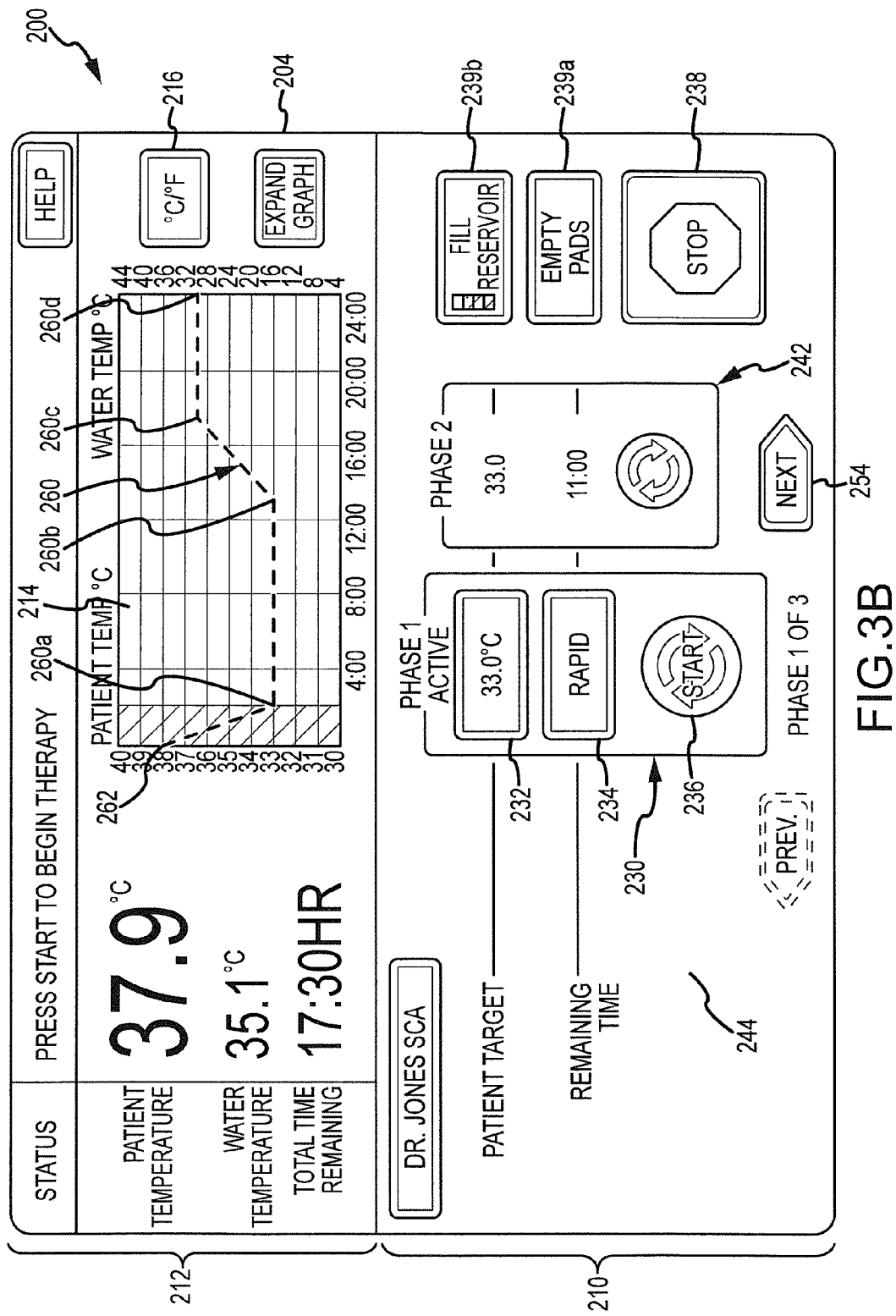

With reference to FIG. 3B, an interface screen 204 of user interface 200 is illustrated that presents data comprising a pre-established control protocol corresponding with the protocol option button 220a of FIG. 3A (i.e. entitled "Dr. Jones SCA"). Such protocol includes phase-specific target patient temperature and duration data sets that are presented numerically in a first portion 210 of the user interface 200 and that are presented graphically in a second portion 212 of user interface 200, as will be further described. Prior to the initiation of a given phase, the corresponding phase duration presented in the first portion 210 of user interface 200 may be the value established in the corresponding protocol. After initiation of a given phase, the phase duration presented in the first portion 210 of the interface 200 may be the remaining amount of time, or remaining phase duration, for the given phase.

Each phase-based set of target patient temperature and phase duration data may be selectively modified by a user via interactive buttons 232 and 234 presented in an interactive region 230 of the first portion 210 of user interface 200, e.g. via touch-screen and/or point-and-click functionality. For example, a given data set may be selected and presented in buttons 232 and 234 via user control of interactive buttons 254 and 256, labeled "Next" and "Prev.", respectively, wherein data sets may be scrolled across the first portion 210, i.e. from interactive region 230 to a non-interactive region 242 or non-interactive region 244 (See FIG. 3C). In turn, for a given data set located in active region 230, button 232 may be selected to modify a corresponding target patient temperature and/or button 234 may be selected to modify a corresponding given phase duration, as will be further described.

Interactive region 230 of user interface of 200 may also include an interactive button 236, entitled "Start" and symbolically displayed with arrows in green, for use in starting/restarting a given phase of therapy, e.g. via touch screen and/or point-and-click functionality. Relatedly, user interface 200 may also include an interactive button 238, labeled "Stop" and symbolically displayed in a red octagon, for using in stopping a given phase of therapy. Additionally, in the illustrated embodiment interface buttons 239a and 239b may be provided for user control over specific interconnected thermal exchange system features, e.g. filling of a reservoir with a liquid heat exchange medium that is circulated through pads contacted with a patient for thermal exchange during system operation, and emptying of the liquid thermal exchange medium from such pads (e.g. into the reservoir upon completion of a given patient therapy).

With particular reference to FIG. 3B, a patient target temperature for "Phase 1", i.e. "33.0° C.", is presented in corresponding spatial relation to user interface button 232. Further, a patient target temperature for "Phase 2", i.e. "33.0° C.",is presented in a non-interactive region 242.

Figure 3C:
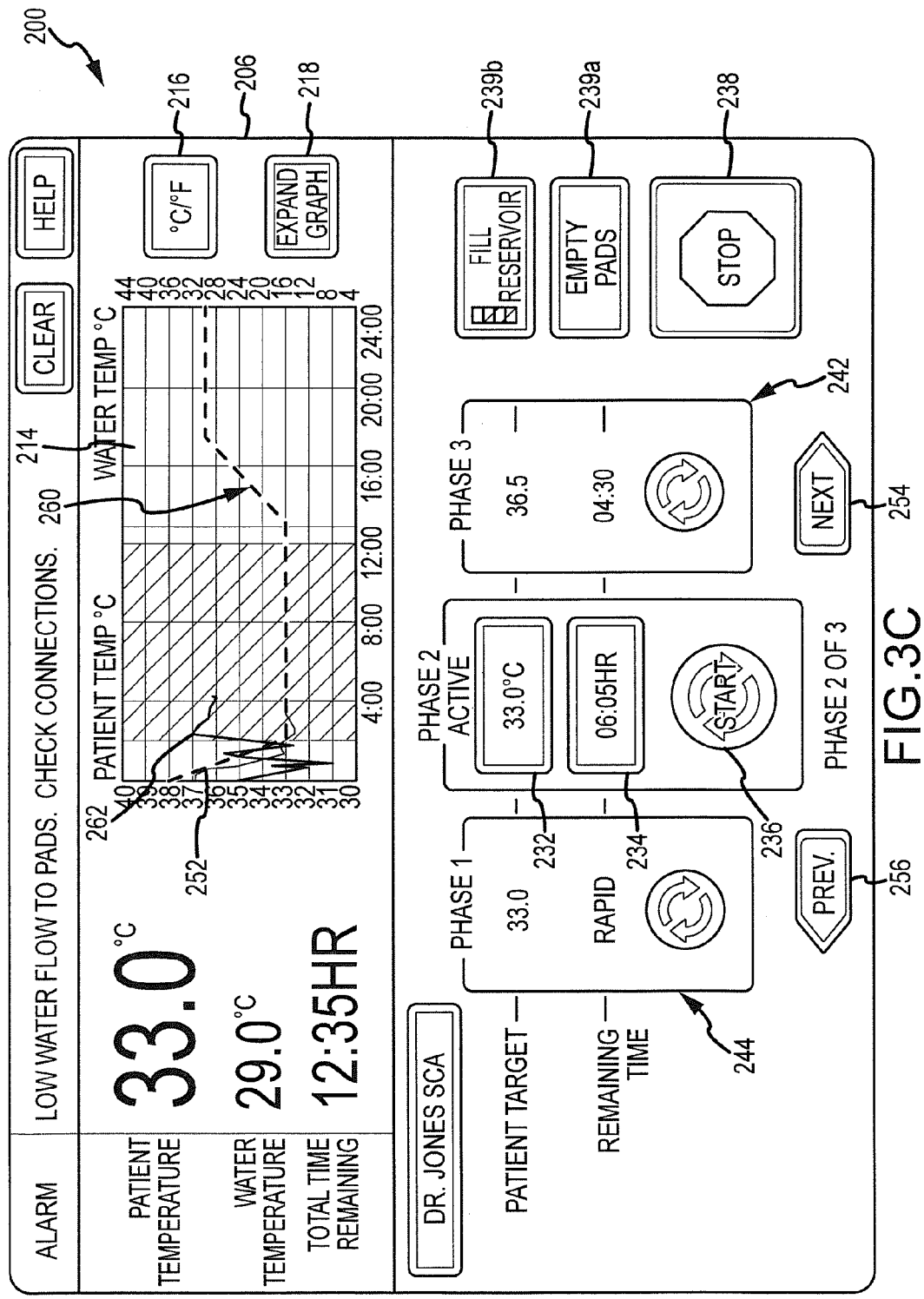
Figure 3D:
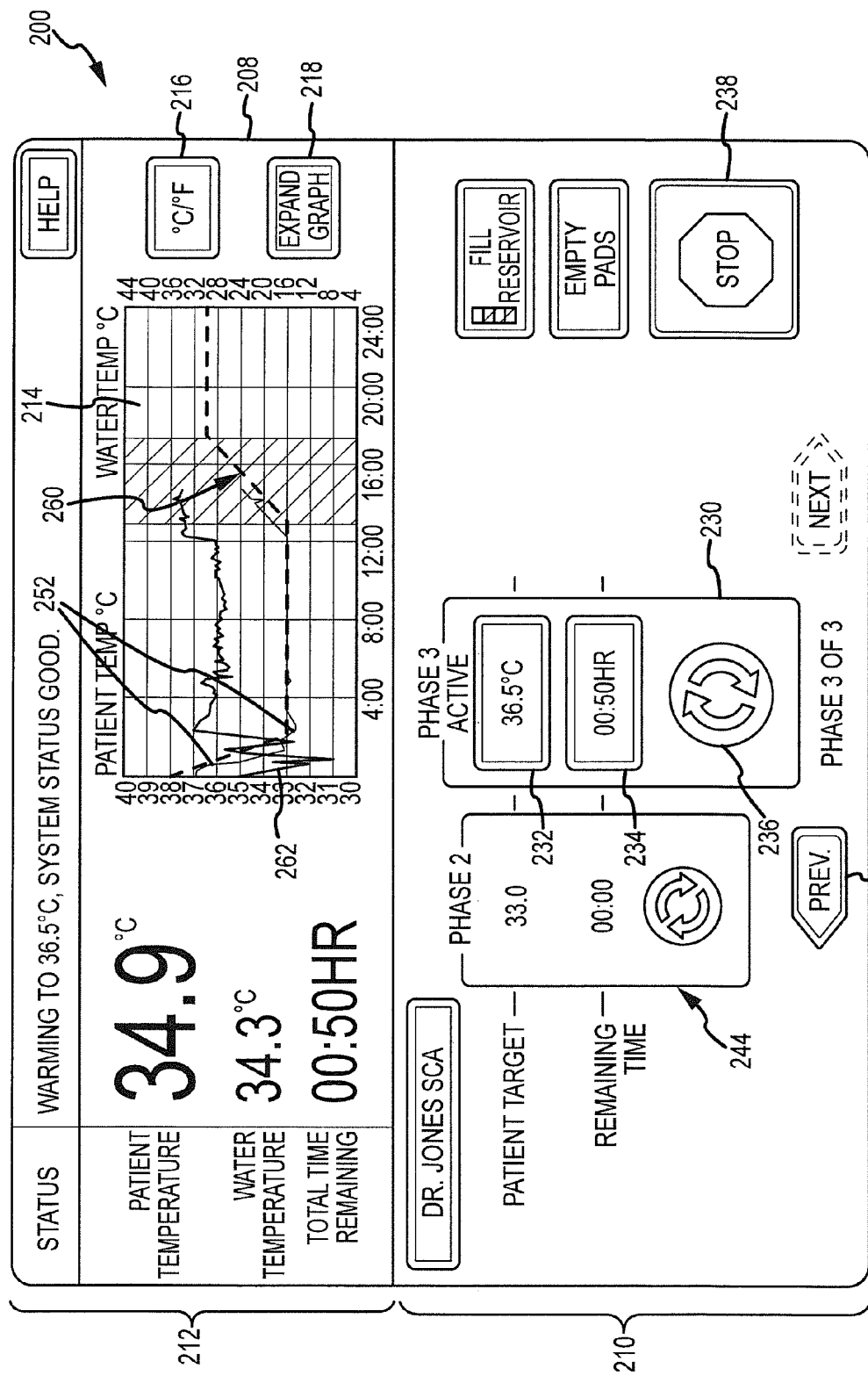

FIG. 3C illustrates an interface screen 206 corresponding with exemplary Phase 2 operations, and FIG. 3D illustrates an interface screen 208 corresponding with exemplary Phase 3 operations. In this regard, interface screen 206 presents a target patient temperature of "33.0° C." for Phase 2 in interactive region 230, and a target patient temperature of "33.0" and "36.5" for "Phase 1" and "Phase 3", respectively, in non-interactive regions 244 and 242, respectively. Similarly, interface screen 208 presents a target patient temperature of "36.5° C." for Phase 3 in interactive region 230, and a target patient temperature of "33.0" for Phase 2 in non-interactive region 244.

Screens 204, 206 and 208 of FIG. 3B, FIG. 3C and FIG. 3D also provide protocol data regarding corresponding set phase durations, or remaining durations, of Phases 1-3. More particularly, in relation to "Phase 2" and "Phase 3", the corresponding set durations of "11:00" and "04:30" are presented in the non-interactive informational region 242 of FIGS. 3B and 3C, respectively. In FIG. 3C the remaining duration of "Phase 2" is illustrated as "6:05 Hr.", since a portion of Phase 2 has already passed (i.e. 4 hours and 55 minutes). Similarly, in FIG. 3D the remaining duration of "Phase 3" is illustrated as "00:50 Hr.", since a portion of Phase 3 has already passed (i.e. 3 hours and 40 minutes).

With respect to FIG. 3B the corresponding phase duration for Phase 1 is a minimum amount of time entailed to lower the temperature of a given patient to the target patient temperature for "Phase 1", i.e. 33.0° C., with the system operating at pre-set maximum rate. As such, the duration information corresponding with "Phase "1 is presented in duration button 236 as "Rapid".

As noted above, phase-specific target patient temperature and phase duration data sets may be presented graphically in a second portion 212 of user interface 200, as reflected by FIG. 3B, FIG. 3C and FIG. 3D. In this regard, the phase-specific target patient temperature and phase duration data may be utilized to generate a plot of a target patient temperature level as a function of time-in-therapy. This may be characterized as a target patient temperature adjustment rate. For example, and as shown in FIG. 3B, FIG. 3C, and FIG. 3D a temperature-to-time graphic display region 214 may illustrate a target patient temperature plot 260 (e.g. a dashed line), wherein an interactive button 216 may be utilized to control the units of temperature display, i.e. ° C. or ° F.

In relation to the target patient temperature plot 260, a first target patient temperature for Phase 1 corresponds with the location of a first plot point 260a, a second target patient temperature and a corresponding phase duration for Phase 2 correspond with the location of a second plot point 260b, a third target patient temperature and corresponding phase duration for Phase 3 correspond with the location of a third plot point 260c, and a fourth target patient temperature for a final phase corresponds with the location of a fourth plot point 260d. In relation to Phase 1, the target patient temperature plot portion, or slope, may be generated based upon a starting, measured patient temperature, the Phase 1 target patient temperature, and a predicted rate of cooling for Phase 1 operations based upon known system cooling parameters. In short, the plot position for Phase 1 reflects a predicted patient temperature adjustment rate.

As illustrated in FIG. 3B, FIG. 3C and FIG. 3D, user interface 200 may also be provided to numerically display a measured patient temperature on an ongoing basis in the second portion 212. Similarly, user interface 200 may be provided to numerically present a measured water temperature (e.g. as employed as a thermal exchange medium) on an ongoing basis.

In this regard, user interface 200 may be adapted to graphically present, or plot, the measured patient and water temperatures on an ongoing basis in the graphic display region 214. By way of example, FIG. 3C and FIG. 3D illustrate a measured patient temperature plot 252 (e.g. a relatively thin line) and a measured water temperature plot 262 (e.g. a relatively thick line), both in time-based relation to the target patient temperature plot 260. Further, the graphic display region 214 may be selectively expanded via user interface with a button 218 entitled "EXPAND GRAPH", wherein the plots 252, 260 and 262 may be displayed in relation to an expanded graph. Additionally, the graphic display region 214 may be provided to visually indicate which of a plurality of therapy phases is currently in process. For example, in FIG. 3B a portion of the graphic display region 214 may be presented in a different manner (e.g. a different color) than the rest of the display (e.g. as indicated by angled lines in FIG. 3B) to indicate that "Phase 1" has been or is about to be initiated. Similarly, in FIG. 3C a portion of graphic display region 214 visually indicates that "Phase 2" is currently-in-process (e.g. via a different color than the rest of the display as reflected by the diagonal lines of FIG. 3C), and in FIG. 3D graphic display region 214 visually indicates that "Phase 3" is underway.

Of note, the measured patient temperature plot 252 and target patient temperature plot 260 may each be graphically presented in corresponding unit relation to a first temperature scale, i.e. "PATIENT TEMP ° C." as provided along the left side of the graphic display region 214. Such corresponding unit relationship may be further visually highlighted for a user by presenting the "PATIENT TEMP ° C." indicator and temperature unit measures, e.g. "30" to "40" in FIG. 3C in a color (e.g. yellow) or other unique manner that corresponds with the color (e.g. yellow) or other unique manner of display for the measured patient temperature plot 252 and target patient temperature plot 260.

Further, the measured water temperature plot 262 may be graphically presented in corresponding unit relation to a second temperature scale, i.e. "WATER TEMP ° C.", as provided along the right side of the graphic display region 214. Such corresponding unit relationship may be further visually highlighted for a user by presenting the "WATER TEMP ° C." indicator and temperature unit measures, e.g. "4" to "44" in FIG. 3C, in a color (e.g. blue) or other unique manner that corresponds with the color (e.g. blue) or other unique manner of display for the measured water temperature plot 262, and that is otherwise different from the color (e.g. yellow) or manner of display for the measured patient temperature plot 252, target patient temperature plot 262 and their corresponding unit indicators.

Of further note, it may be noted that the scaling of the above-noted unit temperature measures along the left side and right side of the graphic display region 214 may be different. Such difference in scaling accommodates differences between the measured/target patient-related temperature indicator and the measured water-related temperature indicators. For example, in relation to FIG. 3C, the measured/target patient related-temperature indicator range is from 30° C. to 40° C., while the measured water related-temperature indicator range is from 4° C. to 44° C. By accommodating such range differences, the measured and target patient-related temperature plots may more noticeably reflect smaller degrees of temperature change. More generally, and as may be appreciated, many of the other display capabilities described above facilitate user visual monitoring and attendant responsive control of a patient therapy session.

Figure 3E:
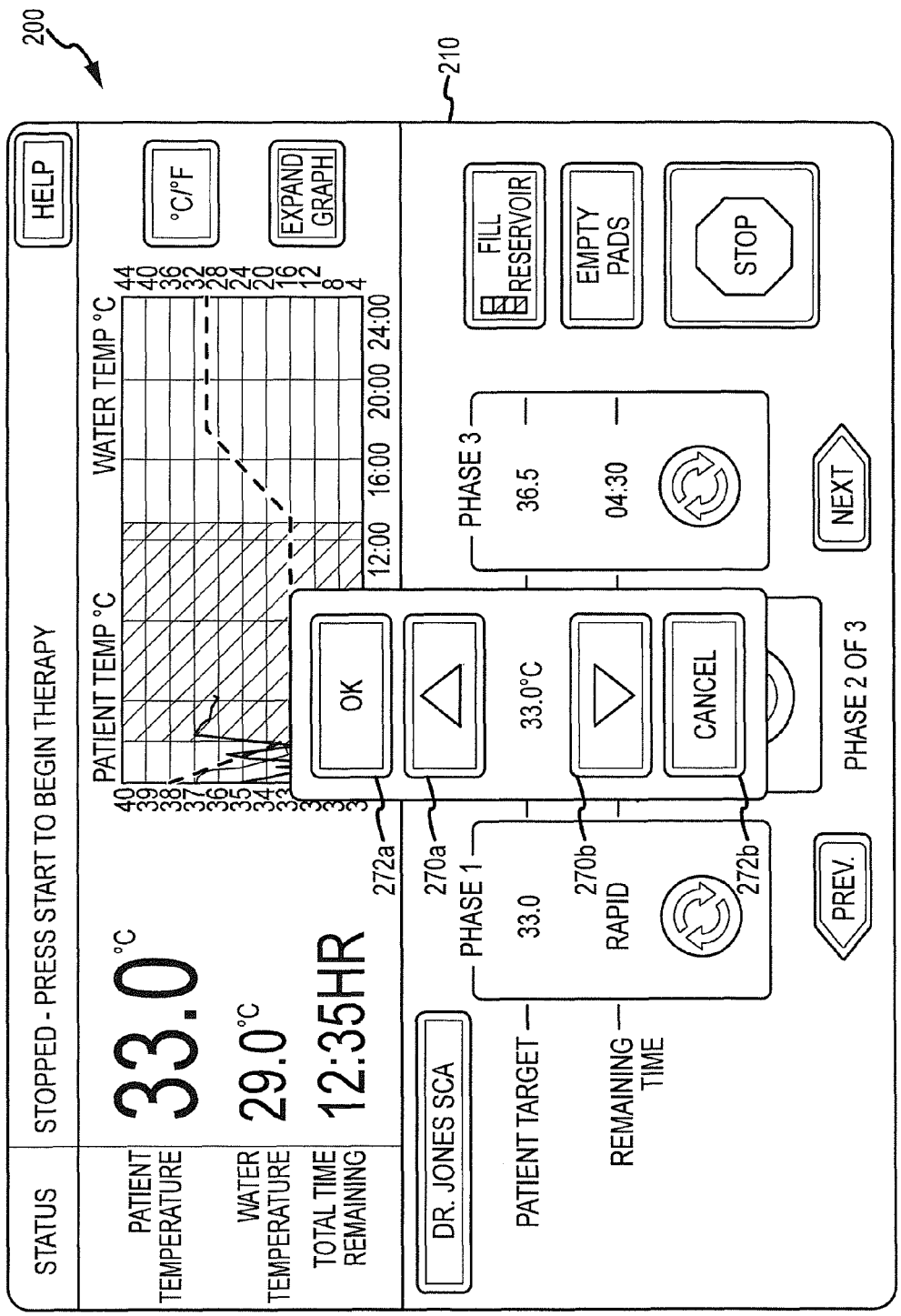

In this regard, and as previously noted, the phase-specific target patient temperature and phase duration data of a given protocol may be modified in a given case utilizing buttons 232 and 234, respectively. For example, when button 232 illustrated in FIG. 3B is selected by a user, a screen 210 may be displayed as shown in FIG. 3E. In turn, magnitude control buttons 270a, 270b may be utilized to change the target patient temperature for Phase 2 to a desired magnitude, and then applied or cancelled via selection of button 272a entitled "OK" or button 272b entitled "Cancel".

Figure 3F:
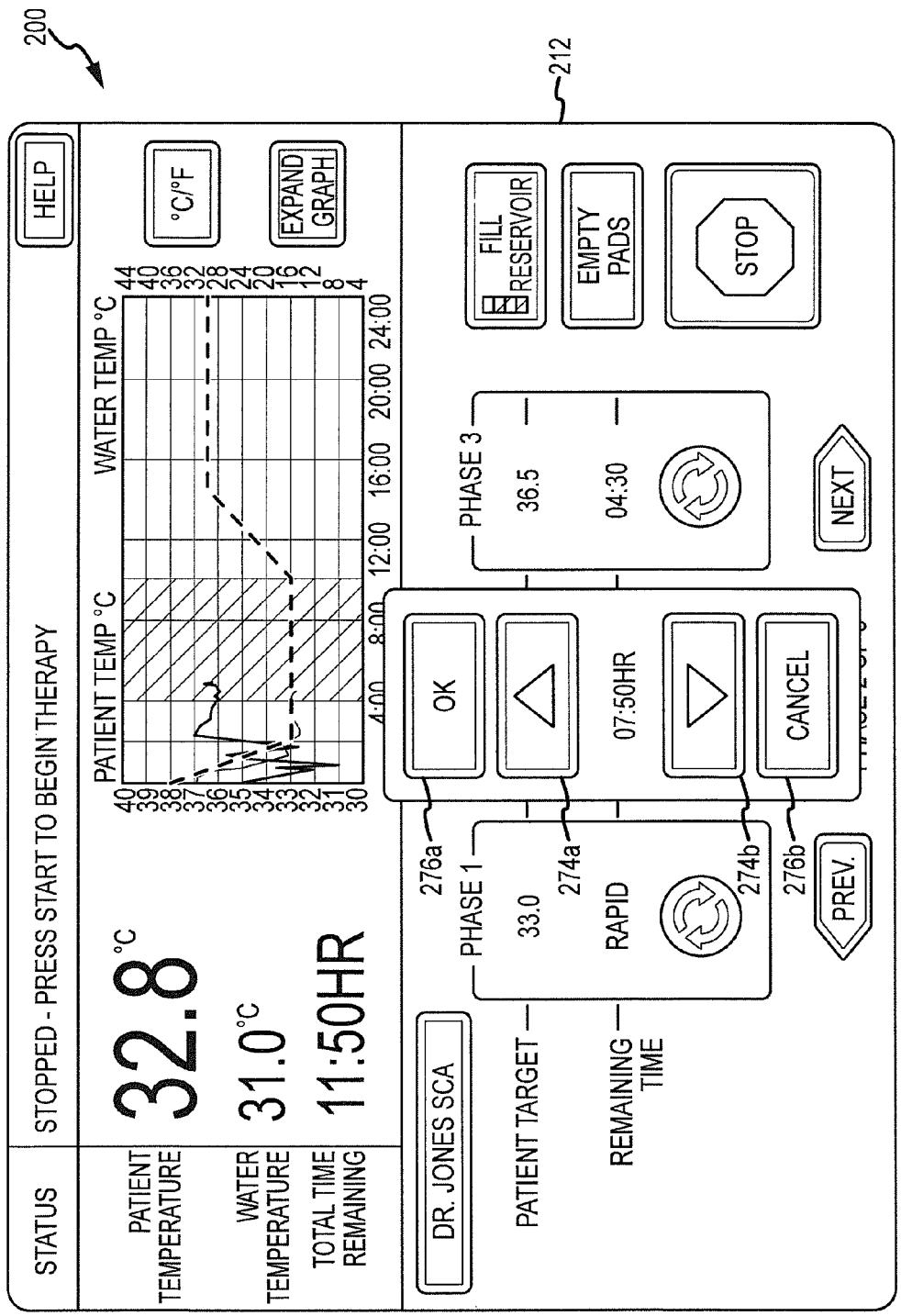

Similarly, when button 234 illustrated in FIG. 3B is selected by user, a screen 212 may be displayed as shown in FIG. 3F. In turn, magnitude control button 274a, 274b may be utilize to change the phase duration of Phase 2 and then applied or cancelled via selection of button 276a entitled "OK" or button 276b entitled "Cancel". Upon modification of target patient temperature protocol data or a phase duration protocol data by a user, the interconnected programmable multi-phase control module will control the cooling/heating of the thermal exchange medium in accordance with the modified protocol data. Correspondingly, the user interface 200 may be adapted so that the target patient temperature plot 260 on the graphic display 214 will automatically reflect such changes.

Figure 3G:
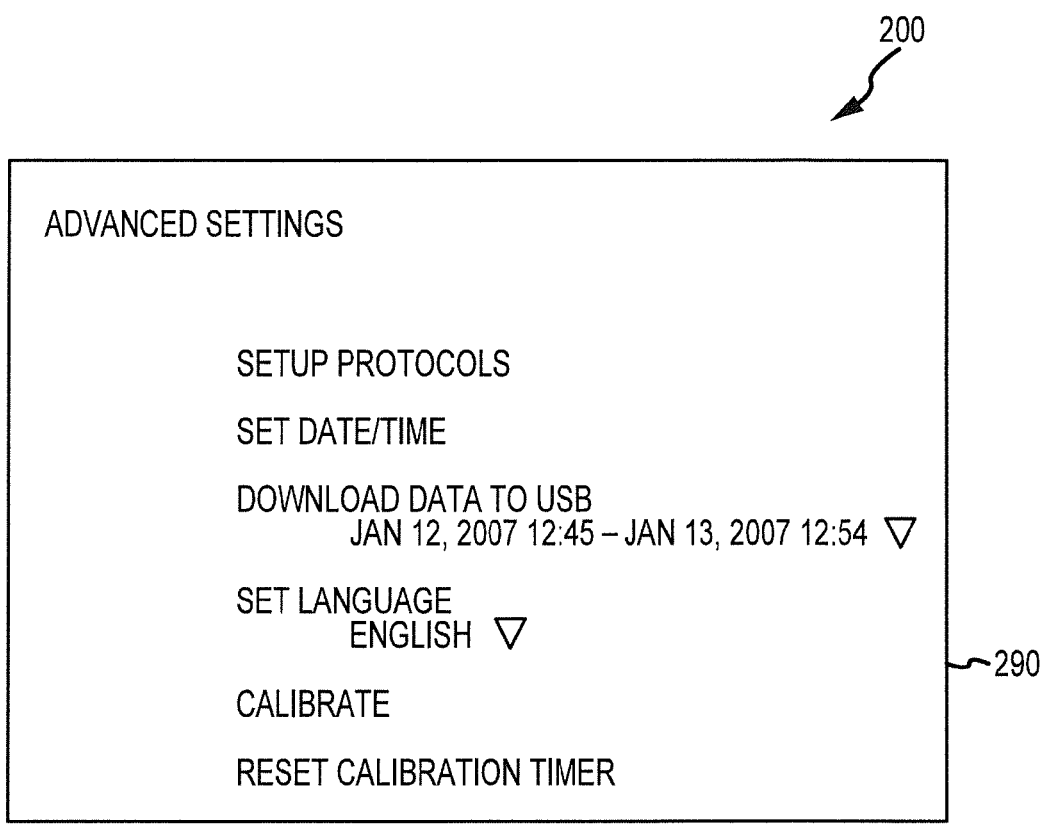

Returning now to FIG. 3A, interactive screen 202 includes an interactive button 222 entitled "Advanced Set-Up" for use in establishing one or more protocols. In particular, upon user selection of the interactive button 222, an interactive screen 290 may be presented as illustrated in FIG. 3G. In turn, upon user selection of a given menu list item by a user (e.g. via touch screen or point-and-click functionality), further corresponding screens may be presented. For example, upon selection of the menu item "Set-Up Protocols", a user may access a plurality of screens to establish a name of a protocol, and corresponding control data and alarm condition data on a phase-specific basis.

In this regard, control functionality may be included in various embodiments that provides for the establishment of a protocol to facilitate phase-specific patient therapy in one of either a manual mode or an automatic mode of operation for each given phase of patient treatment. In one embodiment, subsequent to selection of the "Set-Up Protocols" menu item of screen 290 of FIG. 3G, a user may proceed to establish control and alarm condition data for a given phase (e.g. Phase 1, Phase 2 etc.) wherein a pop-up window may be presented (not shown) that allows a user to select one of either an "Automatic" mode or a "Manual" mode of operation for the given phase.

By way of example, upon selection of a "Manual" mode option for Phase 1 operation, a screen 292 may be presented as shown in FIG. 3H. More particularly, interactive screen 292 may be provided to receive user input parameters in a plurality of fields 280a, corresponding with a plurality of data types indicated by corresponding data field names 282a. In the later regard, the data field names 282a, may be displayed in a manner that prompt a user to input corresponding data into fields 280a, (e.g., by blinking and/or being displayed in a preset color until the data is entered).

In the illustrated embodiment of FIG. 3H, two optional pre-set conditions may be set by a user in relation to Phase 1—Manual mode operations. First, a user may establish a first condition, e.g. via selection of a "Y" option as opposed to a "N" option, to automatically switch from Phase 1—Manual mode operation to a next phase of operation, e.g. Phase 2, upon the expiration of a set duration of Manual mode operation. In the illustrated embodiment, such "Duration" has been inputted as protocol data by a userto be "1:00 Hr.". As further illustrated, a second condition may be selected by a user, e.g. the selection of "Y" as opposed to a "N" option, to automatically switch from the Phase 1—Manual mode of operation to a next phase of operation, e.g. Phase 2, upon system receipt and processing of a measured patient temperature signal that indicates that a patient has "stabilized" in terms of physiological temperature response.

As further reflected by FIG. 3H, a user may input control data establishing a target temperature for a thermal exchange medium, e.g. a water target temperature, wherein during the Manual mode a patient temperature control system will cool/heat the thermal exchange medium at a predetermined maximum rate to reach the set thermal exchange medium temperature (e.g. "4.0 C" for the "Water target"), and will continue to operate at the set temperature until the mode is terminated.

Upon user selection of an "Automatic" mode option for Phase 1 operation, a user a screen 294 may be presented as shown in FIG. 3I. More particularly, interactive screen 294 may be provided to receive user input parameters in a plurality of fields 280b, corresponding with a plurality of data types indicated by corresponding data field names 282b. In the later regard, the data field names 282b may be displayed in a manner that prompt a user to input corresponding data into fields 280b (e.g., by blinking and/or being displayed in a preset color until the data is entered).

By way of example, the input parameters may include protocol control data to set a patient target temperature, e.g. the patient target temperature of Phase 1 in the displayed embodiment has been set by a user at "33.0° C.", and a set phase "Duration". Further, the user interface 200 may provide for user input regarding automatic termination of Phase 1—Automatic mode and initiation of Phase 2 operations upon one of two alternate pre-set condition(s) being met. First, a user may establish a first pre-condition (e.g., via selection of a "T" option), to automatically "jump" from Phase 1—Automatic mode operation to Phase 2 operation when a measured patient temperature reaches the protocol patient target temperature for Phase 1, i.e., "37.0 C". Alternatively, a user may establish a second pre-condition, e.g., via selection of a "D" option, to jump from Phase 1—Automatic mode operation to Phase 2 operation upon the expiration of the protocol set duration of Phase 1. In the illustrated embodiment, such set duration has been inputted by the user to be "6:00 Hr". Alternatively, a user may establish, e.g. via selection of a "N" option, that automatic jumping is not desired.

As further reflected by FIGS. 3H and 3I, user interface 200 may be further provided to allow for user input to establish phase-specific, e.g. phase-mode-specific, alarm condition data. In particular, in relation to the Phase 1—Manual mode of operation, a patient high temperature alert level, e.g., "40.0 C", and a patient low temperature alert level, e.g., "33.0 C" may be set. Similarly, in relation to the Phase 1—Automatic mode of operation, a patient high temperature alert level, e.g. "40.0 C", and a patient low temperature alert level, e.g. 33.0 C" may be set. In turn, during a given mode when a measured patient temperature signal goes outside of the corresponding high/low range of patient temperature, user interface 200 may be adapted to provide an alert output to a user. For example, a pop-up window and/or audible output alert may be provided to a user that not only alerts the user to the presence of an alarm condition, but also informs the user as to the particular condition and identifies potential remedial user response options. Such functionality may be extended to thermal exchange medium temperature limits, e.g. water high temperature and water low temperature, alarm condition alert levels for application in Phase 1—Automatic mode operations, as indicated in FIG. 3H.

In addition to Phase 1 protocol control and alarm condition data, it should be appreciated that the user interface 200 may provide additional screens similar to screens 292 and 294 that provide for the entry of protocol control data and alarm condition data for one or more additional phases of operation. In this regard, a user may pre-establish data for multiple phases, as may be desired by a given practitioner.

FIGS. 4A-4D illustrate selected aspects of another embodiment of an interactive user interface 300 operatively interconnected to a programmable control module (e.g. module 20 of FIG. 1) for providing phase-related control and alarm data, and measured data, to a user and for interfacing with a user to receive control input via various interactive screen displays. This embodiment contemplates an implementation of the present invention directed to two alternative patient therapy protocols, i.e. for normothermia therapy and for hypothermia therapy (e.g. for use in treating stroke, cardiac arrest and/or traumatic brain injury). Again, such embodiments are described for purposes of illustration and additional embodiments will be apparent to those skilled in the art.

Figure 4A:
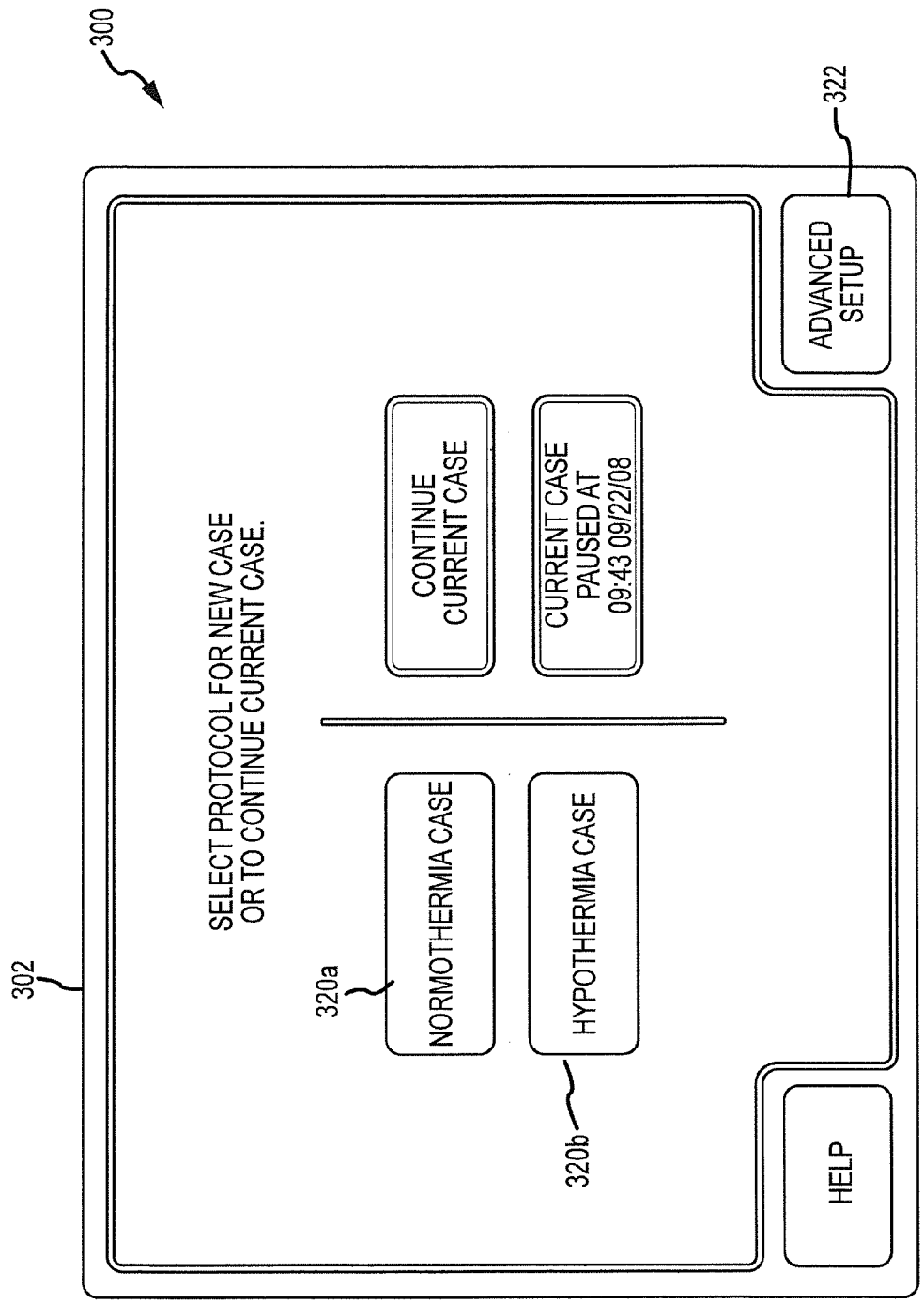
FIGS. 4A-4D illustrate exemplary screens of another embodiment of a user interface employable in the system embodiment of FIG. 1 and method embodiment of FIG. 2.

With particular reference to the interactive screen 302 of user interface 300 illustrated in FIG. 4A, two alternate protocol options may be presented to a user for use in a given therapy procedure. As shown, the two alternate options are entitled "NORMOTHERMIA CASE" and "HYPOTHERMIA CASE", wherein a user may select a given one of the two options utilizing buttons 320a or 320b, e.g. via touch-screen and/or point-and-click functionality.

Figure 4B:
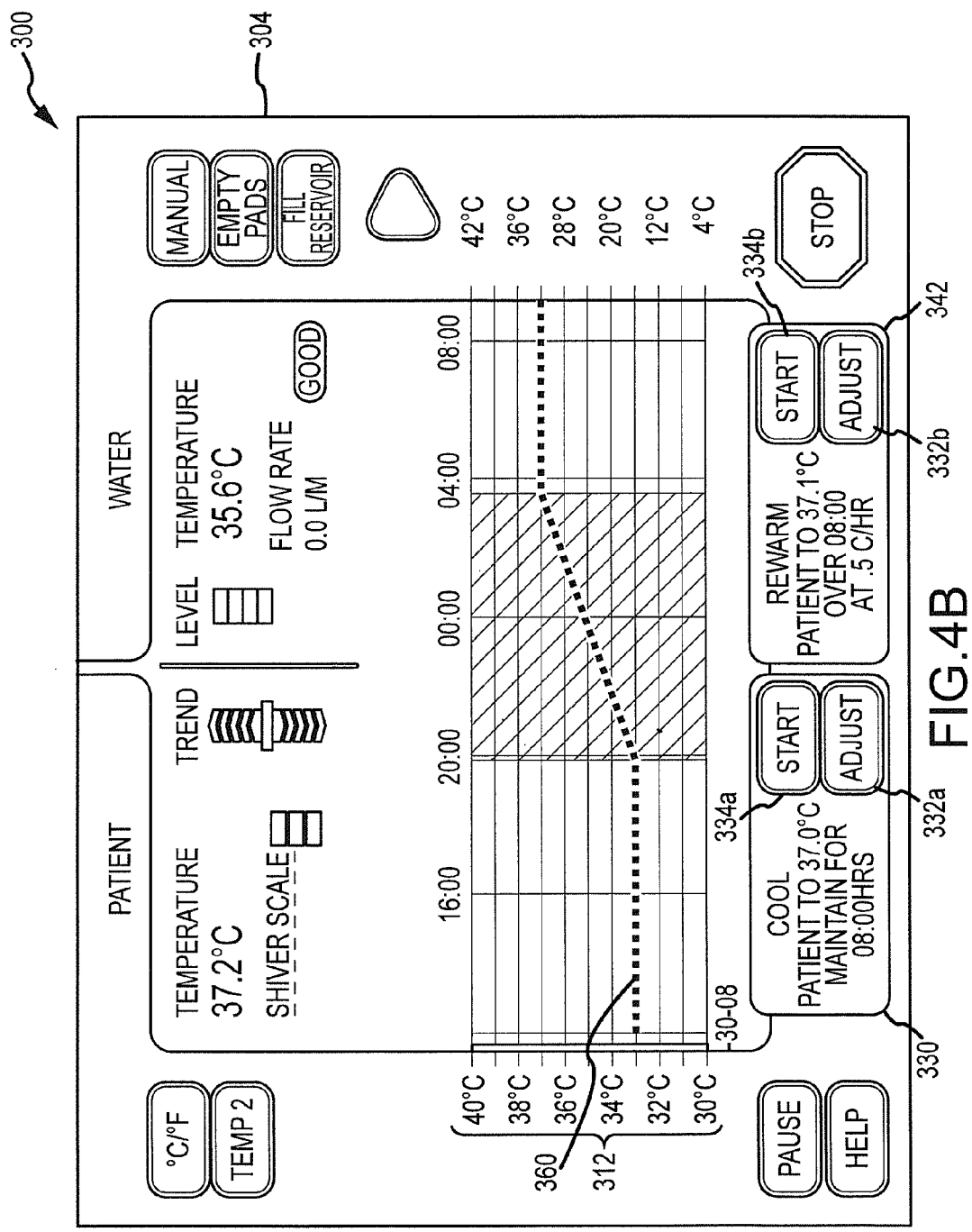
Figure 4C:
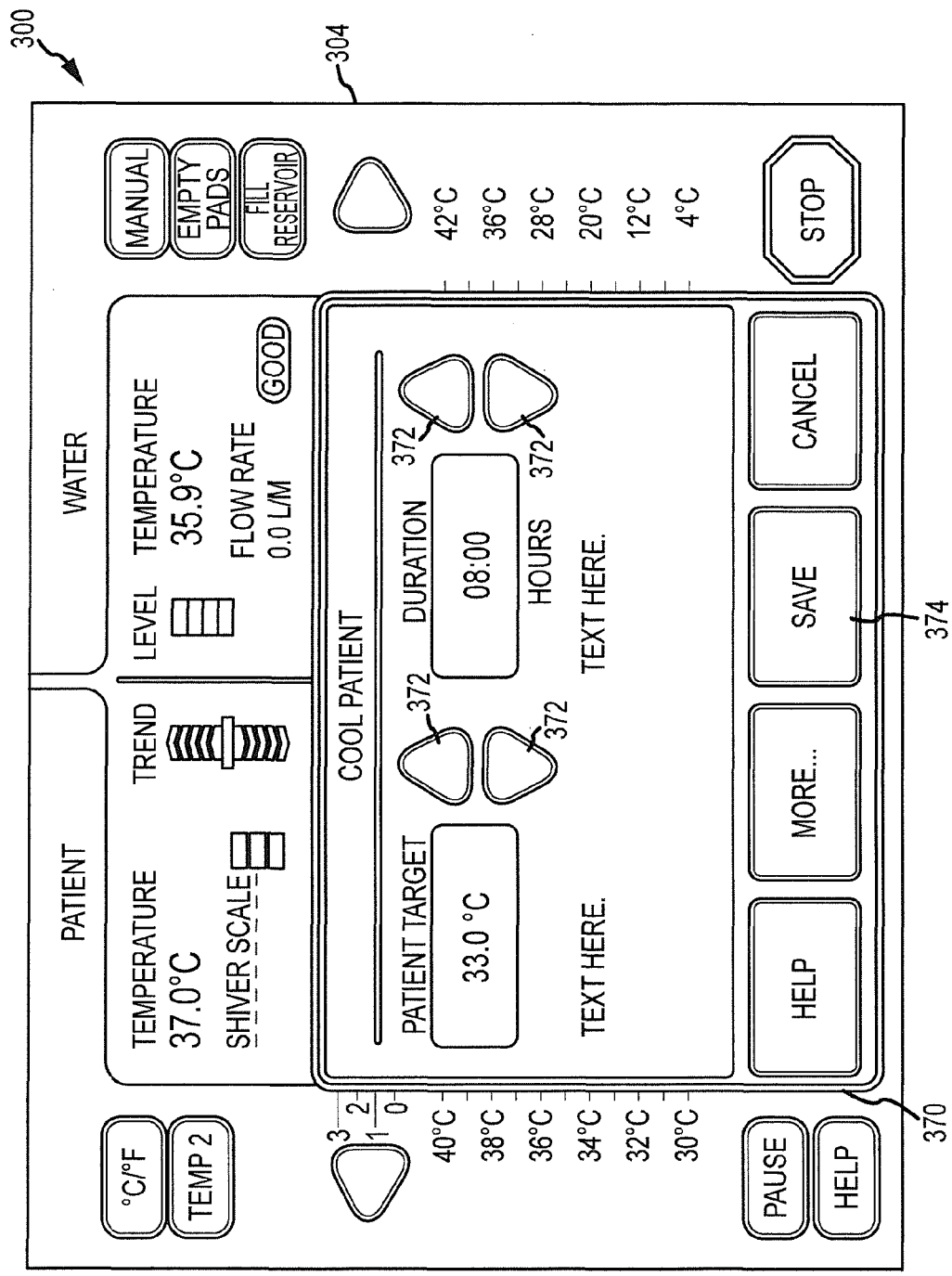

With reference to FIG. 4B, an interface screen 304 of user interface 300 is illustrated that presents data comprising a pre-established control protocol corresponding with the protocol option button 320b of FIG. 4A (i.e. entitled "HYPOTHERMIA CASE"). Such protocol includes two phase-specific target patient temperature and duration data sets that are presented numerically in interactive display regions 330 and 342 of user interface 300.

Each phase-based set of target patient temperature and phase duration data may be selectively modified by a user via interactive buttons 332a and 332b, as presented in the interactive regions 330 and 342, via touch-screen and/or point and click functionality. More particularly, a given data set may be adjusted utilizing button 332a or 332b entitled "ADJUST", and immediately applied utilizing button 334a or 334b entitled "START". In the former regard, for example, for the cooling phase corresponding with interactive region 330, the corresponding target patient temperature and phase duration data may be adjusted via user interface with button 332a to access pop-up window 370 shown in FIG. 4C. In turn, control buttons 372 may be utilized to adjust the parameters and control button 374 entitled "SAVE" may be employed to save the adjusted parameters.

With further reference to FIG. 4B, phase-specific target patient temperature and phase duration data may be utilized to generate a target patient temperature adjustment rate plot 360 that is presented graphically in a graphic display region 312 of the user interface 300. As may be appreciated, measured patient temperature data and measured water temperature data may also be numerically displayed and utilized to generate corresponding plots for display in the graphic display region 312, in a manner analogous to that described in relation to the embodiment of FIGS. 3A-3I addressed above. Further, the graphic display region 312 may visually highlight a phase that is currently in process, e.g. via color differentiation for such phase in corresponding relation to a color utilized in the phase-oriented interaction regions 330 and 342.

Figure 4D:
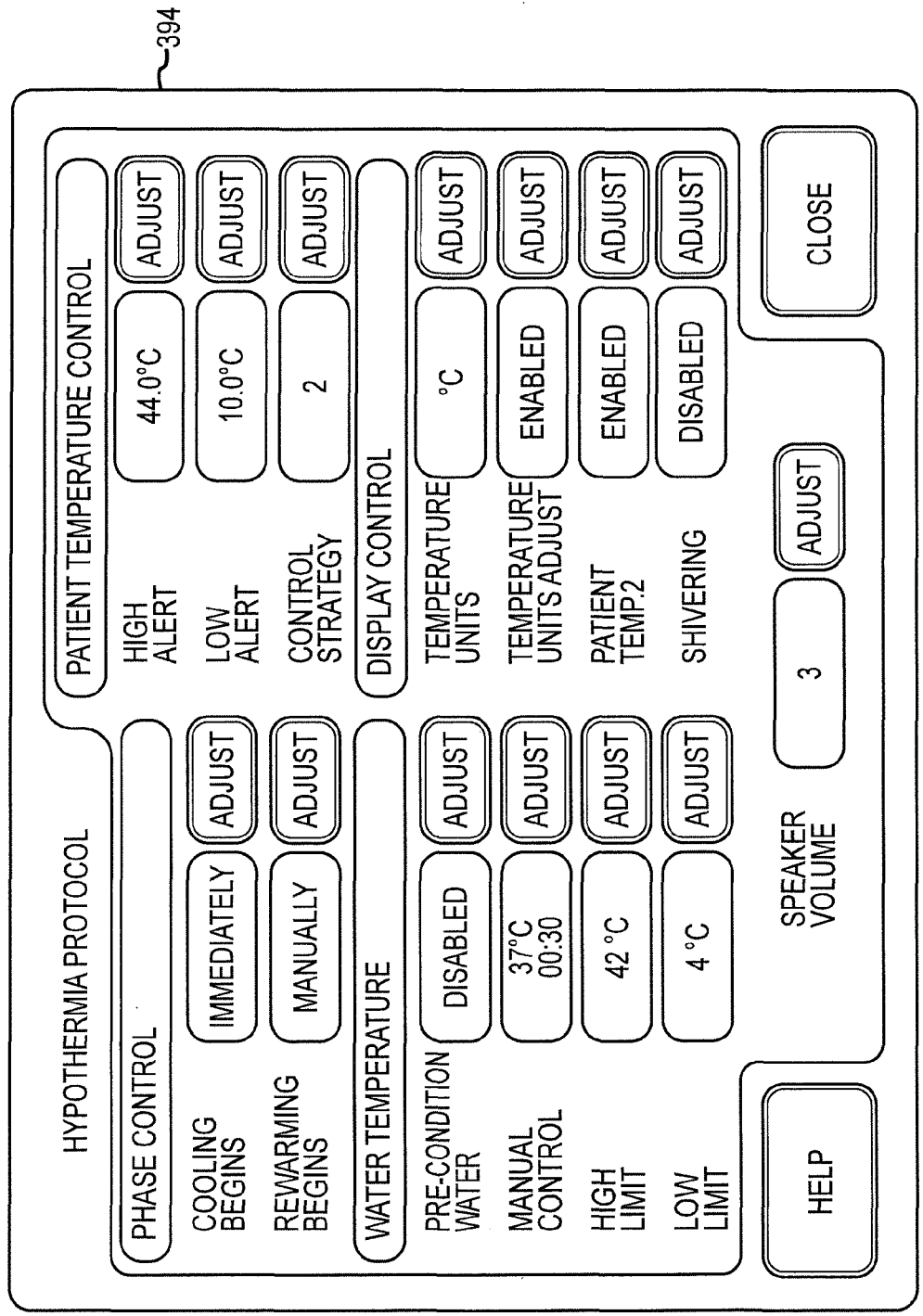

Reference is again made to FIG. 4A, wherein interactive screen 302 includes an interactive button 322 entitled "ADVANCED SET-UP" for use in establishing the two optimal protocols. In particular, upon selection of the interactive button 322, an interactive screen 390 may be presented as illustrated in FIG. 4D. In turn, the various interactive control buttons presented on screen 394 may be utilized to establish parameters and protocol control data in a manner analogous to that described above in relation to FIGS. 3G, 3H and 3I. In this regard, such user control may be facilitated via the consistent intuitive use of an "ADJUST" button to access pop-up windows that are easy to employ, as per the pop-up window shown in FIG. 4C above.

The various embodiments described above are for purposes of illustration and are not intended to limit to scope of the present invention.

What is claimed is:

1. A method for controlling a temperature of a thermal exchange medium of a patient temperature control system, comprising:
    establishing a programmed protocol in response to user input at a user interface for each of a plurality of phases that are non-overlapping in time, said plurality of phases including at least two successive phases, wherein a target patient temperature is established in response to said user input for each of said plurality of phases, and wherein a set phase duration is established in response to said user input for at least one of said plurality of phases;
    receiving a sensor output signal of a measured patient temperature on an ongoing basis, wherein said measured patient temperature is a measured core body temperature; and,
    controlling automatically a temperature of a thermal exchange medium of a patient temperature control system, based at least in part upon said programmed protocol, during at least a portion of each of said plurality of phases, wherein for each given phase of said plurality of phases said controlling comprises comparing said measured patient temperature to said corresponding target patient temperature for said given phase, and wherein said controlling further comprises both automatically terminating and initiating together, respectively, a first phase and a second phase of said at least two successive phases upon a determination by said comparing that said measured patient temperature has reached the target patient temperature for said first phase of said at least two successive phases.

2. A method as recited in claim 1, wherein for said at least a portion of each of said plurality of phases said controlling step further comprises:
    setting automatically said temperature of the thermal exchange medium based at least in part upon said measured patient temperature and said corresponding target patient temperature comprising said programmed protocol.

3. A method as recited in claim 1, said establishing step further comprising:
    establishing said programmed protocol in response to user input at said user interface to comprise different target patient temperatures for at least a first set of two of said plurality phases.

4. A method as recited in claim 3, said establishing step further comprising:
    establishing said programmed protocol in response to user input at said user interface to comprise the same target patient temperatures for at least a second set of two of said plurality of phases.

5. A method as recited in claim 4, wherein said plurality of phases comprises at least three successive phases, and wherein said phases comprising said first set of two of said plurality of phases are successive and automatically terminated and initiated together, and said phases comprising said second set of two of said plurality of phases are successive and automatically terminated and initiated together.

6. A method as recited in claim 1, wherein said at least one of said plurality of phases is said second phase of said at least two successive phases, said establishing step further comprising:
    establishing said programmed protocol in response to said user input at said user interface to comprise a set phase duration for at least another one of said plurality of phases; and, wherein said controlling further comprises both automatically terminating and initiating together, respectively, said second phase and said at least another phase of said plurality of phases upon expiration of said set phase duration for said second phase of said plurality of phases.

7. A method as recited in claim 6, wherein for said at least another one of said plurality of phases, said controlling step further comprises:
    setting automatically said temperature of the thermal exchange medium based at least in part upon both said corresponding set phase duration and said corresponding target patient temperature comprising said programmed protocol.

8. A method as recited in claim 1, said establishing step further comprising:
    receiving said user input in predetermined computerized record fields.

9. A method as recited in claim 1, said establishing step further comprising:
    repeating said establishing step to establish a plurality of programmed protocols; and
    providing said user interface for user selection of one of said plurality of programmed protocols for use in said controlling step.

10. A method as recited in claim 1, further comprising:
    outputting to a user at said user interface, during at least a portion of at least any one of said plurality of phases, information based upon:
    a target patient temperature adjustment rate for said at least any one of said plurality phases; and,
    at least one of the following:
    said ongoing measured patient temperature; and
    an ongoing measured temperature of said thermal exchange medium.

11. A method as recited in claim 10, said outputting step comprising:
displaying said information at said user interface.

12. A method as recited in claim 11, said displaying step comprising:
presenting said information in a plurality of different plots, wherein each of said plurality of different plots are presented on a graphic temperature/time scale basis.

13. A method as recited in claim 10, further comprising:
determining automatically said target patient temperature adjustment rate based at least in part upon said programmed protocol.

14. A method as recited in claim 10, further comprising one of the following:
determining automatically said target patient temperature adjustment rate based at least in part on said target patient temperatures comprising said programmed protocol for successive ones of said plurality of phases; and
determining automatically said target patient temperature adjustment rate based at least in part on said target patient temperature for said at least one of said plurality of phases and said measured patient temperature.

15. A method as recited in claim 1, further comprising:
outputting to a user at said user interface, during at least a portion of said at least two successive phases, information based upon:
a target patient temperature adjustment rate for said at least two successive phases; and,
at least one of the following:
said ongoing measured patient temperature; and
an ongoing measured temperature of said thermal exchange medium; wherein said information is presented in a plurality of different plots, wherein each of said plurality of different plots are presented on a graphic temperature/time scale basis.

16. A method as recited in claim 1, further comprising:
modifying said programmed protocol for at least one of said plurality of phases, after said establishing step, in response to user input at said user interface prior to completion of said at least one of said plurality of phases; and
using automatically said modified programmed protocol in said controlling step in completing said at least one of said plurality of phases.

17. A method as recited in claim 16, said modifying step comprising:
displaying at said user interface at least one of said target patient temperature and said set phase duration for said at least one of said plurality of phases;
providing an interactive user control for direct modification and display, in response to user input at user interface, of said at least one of said target patient temperature and said set phase duration for said at least one of said plurality of phases.

18. A method as recited in claim 1, said establishing further comprising:
setting at least one alarm condition specific to at least any one and less than all of said plurality of phases in response to user input at said user interface; and
monitoring automatically a condition corresponding with said at least one alarm condition during said at least any one and less than all of said plurality of phases.

19. A method as recited in claim 18, further comprising:
providing automatically an alarm output to a user in response to said monitoring step during said at least any one and less than all of said plurality of phases.

20. A method for controlling a temperature of a thermal exchange medium of a patient temperature control system, comprising:
establishing a plurality of programmed protocols, wherein for each one of the plurality of programmed protocols a corresponding protocol is established in response to user input at a user interface for each of a corresponding plurality of phases that are non-overlapping in time, each of said corresponding plurality of phases including at least two successive phases, wherein a target temperature is established for at least one of said corresponding plurality of phases, and wherein a set phase duration is established for at least one of said corresponding plurality of phases,
receiving a sensor output signal of a measured patient temperature on an ongoing basis, wherein said measured patient temperature is a measured core body temperature; and,
controlling automatically a temperature of a thermal exchange medium of a patient temperature control system based at least in part upon the programmed protocol corresponding with a selected one of said plurality of programmed protocols, wherein for each given phases of said corresponding plurality of phases for the selected one of said plurality of programmed protocols said controlling comprises comparing said measured patient temperature to said corresponding target patient temperature for said given phase, and wherein said controlling comprises both automatically terminating and initiating together, respectively, a first phase and a second phase of said corresponding at least two successive phases upon a determination by said comparing that said measured patient temperature has reached the target temperature for said first phase of said at least two successive phases.

21. A method as recited in claim 20, further comprising:
providing a user interface adapted for user selection of said selected one of the plurality of programmed protocols for use in said controlling step.

22. A method as recited in claim 20, wherein for each one of the plurality of programmed protocols said one of said corresponding plurality of phases is said second one of said at least two successive phases of said corresponding plurality of phases, and wherein said selected one of said plurality of programmed protocols comprises a set phase duration for another one of said corresponding plurality of phases.

23. A method as recited in claim 20, wherein for each of said plurality of phases corresponding with said selected one of the plurality of programmed protocols said controlling step further comprises:
setting automatically said temperature of the thermal exchange medium based at least in part upon said measured patient temperature and said corresponding target patient temperature.

24. A computer-based system for controlling a temperature of a thermal exchange medium of a patient temperature control system, comprising:
a user interface for receiving user input and providing corresponding output signals; and,
a programmable control module for receiving a sensor output signal of a measured patient temperature that is a measured core body temperature, and for receiving said output signals to establish a programmed protocol by storing control data in corresponding relation to each of a plurality of different patient temperature control phases that are non-overlapping in time, said plurality of different patient control phases including at least two successive phases, wherein a target patient temperature is established in response to said user input at said user interface for each of said plurality of different patient control phases, wherein a set phase duration is established in response to said user input at said user interface for at least one of said plurality of different patient control phases, and wherein said programmable control module comprises control logic for utilizing said stored control data to provide output control signals to a thermal exchanger of a patient temperature control system in corresponding relation to each of said plurality of different patient temperature control phases;

wherein for each given phase of said plurality of different patient temperature control phases said programmable control module control logic is operable to compare a measured patient temperature to said corresponding target patient temperature for said given phase, and wherein said programmable control module control logic is operable to both automatically terminate and automatically initiate together, respectively, a first phase and a second phase of said at least two successive phases upon a determination by said comparison of said measured patient temperature to said corresponding target patient temperature for said given phase that said measured patient temperature has reached the target patient temperature for said first one of said at least two successive phases.

25. A system as recited in claim 24, wherein said programmable control module is operable to store at least two protocols comprising corresponding, different control data, and wherein said user interface is employable by a user to select either of said at least two protocols for use by said programmable control module in generating said output control signals.

26. A system as recited in claim 24, wherein said user interface is employable to modify said control data stored by said programmable control module.

27. A system as recited in claim 24, wherein said user interface includes:
a graphic display to visually present a plot of a target patient temperature adjustment rate based on said stored control data.

28. A system as recited in claim 27, wherein said graphic display is operable to display a plot of said measured patient temperature in corresponding time relation to said plot of said target patient temperature adjustment rate.

29. A system as recited in claim 28, wherein said graphic display is operable to display a plot of a measured temperature of a thermal exchange medium employed in said patient temperature control system in corresponding time relation to said plot of said target patient temperature adjustment rate.

30. A method as recited in claim 1, wherein said plurality of phases includes at least three successive phases, and wherein for a third one of said at least three successive phases, said controlling step further comprises:
setting said temperature of the thermal exchange medium based at least in part upon both a corresponding set phase duration and corresponding target patient temperature comprising said programmed protocol.

31. A method as recited in claim 30, wherein for said third one of said at least three successive phases said controlling step further comprises:
comparing said measured patient temperature to said target patient temperature; and
automatically terminating said third one of said at least three successive phases at least partially in response to said comparing step.

32. A method as recited in claim 8, wherein said establishing step further comprises:
presenting a screen at said user interface in relation to each of the plurality of phases, wherein for each of the plurality of phases said user interface is adapted to receive user input parameters in a plurality of predetermined fields, to establish at least one of a patient high temperature alert level and a patient low temperature alert level, and at least one of a thermal exchange medium high temperature limit and a thermal exchange medium low temperature limit.

33. A method as recited in claim 32, wherein said controlling automatically utilizes an established value for said at least one of a thermal exchange medium high temperature limit and a thermal exchange medium low temperature limit during said first phase.

34. A method as recited in claim 12, wherein said presenting step comprises:
presenting said plurality of different plots in a graphic display region in relation to a common horizontal time scale.

35. A method as recited in claim 34, wherein said presenting step comprises:
presenting said target patient temperature adjustment rate and said ongoing measured patient temperature in relation to a first temperature scale on a first side of said graphic display region; and,
presenting said ongoing measured temperature of said thermal exchange medium in relation to a second temperature scale on a second side of said graphic display region.

36. A method as recited in claim 18, wherein said at least one alarm condition is one of the following:
a patient high temperature alert level; and,
a patient low temperature alert level.

* * * * *

UNITED STATES PATENT AND TRADEMARK OFFICE
CERTIFICATE OF CORRECTION

PATENT NO. : 9,566,185 B2
APPLICATION NO. : 12/250320
DATED : February 14, 2017
INVENTOR(S) : Gary A. Carson, Gary Gruszecki and Robert Proctor It is certified that error appears in the above-identified patent and that said Letters Patent is hereby corrected as shown below:

In the Specification

Column 5, Line 24, delete "temerature" and insert --temperature--
Column 7, Line 24, delete "mgiven" and insert --given--

In the Claims

Claim 20, Column 16, Line 10, after "wherein a target" insert --patient--
Claim 20, Column 16, Line 11, delete "at least one" and insert --each--
Claim 20, Column 16, Line 24, delete "phases" and insert --phase--
Claim 20, Column 16, Line 34, after "reached the target" insert --patient--

Signed and Sealed this
Eleventh Day of April, 2017

Michelle K. Lee
*Director of the United States Patent and Trademark Office*